United States Patent
LeBoeuf et al.

[19]

[11] Patent Number: 5,922,821
[45] Date of Patent: *Jul. 13, 1999

[54] OPHTHALMIC LENS POLYMERS

[75] Inventors: Albert R. LeBoeuf; Mutlu Karakelle, both of Fort Worth, Tex.

[73] Assignee: Alcon Laboratories, Inc., Fort Worth, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/910,923

[22] Filed: Aug. 8, 1997

Related U.S. Application Data

[60] Provisional application No. 60/023,623, Aug. 9, 1996.

[51] Int. Cl.$^6$ .................. C08F 220/20; C08F 212/04; G02C 7/02
[52] U.S. Cl. .................. 526/286; 526/292.5; 526/313; 526/320; 351/159; 351/160 R
[58] Field of Search .................. 526/286, 292.5, 526/313, 320; 351/159, 160 R

[56] References Cited

U.S. PATENT DOCUMENTS

| | | | |
|---|---|---|---|
| 2,976,576 | 3/1961 | Wichterle et al. | 18/58 |
| 3,932,321 | 1/1976 | Maki et al. | 260/17.4 |
| 4,036,814 | 7/1977 | Howes et al. | 260/47 |
| 4,192,685 | 3/1980 | Horike et al. | 430/283 |
| 4,243,790 | 1/1981 | Foley, Jr. | 526/320 |
| 4,304,895 | 12/1981 | Loshaek | 526/313 |
| 4,306,780 | 12/1981 | Tarumi et al. | 526/313 |
| 4,379,874 | 4/1983 | Stoy | 524/27 |
| 4,393,184 | 7/1983 | Tarumi et al. | 526/261 |
| 4,518,756 | 5/1985 | Yoshida et al. | 526/313 |
| 4,528,311 | 7/1985 | Beard et al. | 524/91 |
| 4,573,998 | 3/1986 | Mazzocco | 623/6 |
| 4,578,504 | 3/1986 | Hammar | 560/112 |
| 4,619,657 | 10/1986 | Keates et al. | 623/6 |
| 4,619,662 | 10/1986 | Juergens, Jr. | 623/6 |
| 4,704,006 | 11/1987 | Sakagami et al. | 350/409 |
| 4,731,079 | 3/1988 | Stoy | 623/6 |
| 4,761,438 | 8/1988 | Komiya et al. | 523/106 |
| 4,834,750 | 5/1989 | Gupta | 623/6 |
| 4,919,151 | 4/1990 | Grubbs et al. | 128/898 |
| 5,019,100 | 5/1991 | Hennink et al. | 623/6 |
| 5,224,957 | 7/1993 | Gasser et al. | 623/6 |
| 5,290,892 | 3/1994 | Namdaran et al. | 526/259 |
| 5,364,256 | 11/1994 | Lipscomb et al. | 425/174.4 |
| 5,403,901 | 4/1995 | Namdaran et al. | 526/292.5 |
| 5,416,180 | 5/1995 | Yokoyama et al. | 526/245 |
| 5,442,022 | 8/1995 | Keita et al. | 526/309 |
| 5,470,932 | 11/1995 | Jinkerson | 526/312 |
| 5,545,828 | 8/1996 | Keita et al. | 526/72 |
| 5,556,931 | 9/1996 | Imura et al. | 526/323.1 |
| 5,594,043 | 1/1997 | Nunez et al. | 523/106 |
| 5,702,825 | 12/1997 | Keita et al. | 428/500 |
| 5,708,064 | 1/1998 | Coleman et al. | 524/90 |

FOREIGN PATENT DOCUMENTS

| | | |
|---|---|---|
| 0 273 710 A2 | 7/1988 | European Pat. Off. . |
| 0 330 614 A2 | 8/1989 | European Pat. Off. . |
| 0 485 197 A1 | 5/1992 | European Pat. Off. . |
| 0 488 145 A2 | 8/1992 | European Pat. Off. . |

(List continued on next page.)

OTHER PUBLICATIONS

Acrylens™ "A Technical Evaluation of Foldable Intraocular Lenses" distributed by Ioptex Research, Inc., 1990.

Packard et al., "Poly–HEMA as a Material for Intraocular Lens Implantation: a preliminary report," *Journal of Ophthalmology*, vol. 65, pp. 585–587 (1981).

*Primary Examiner*—Tae Yoon
*Attorney, Agent, or Firm*—Patrick M. Ryan

[57] ABSTRACT

High refractive index copolymers suitable for use in ophthalmic lenses, such as foldable intraocular lenses, are disclosed. The high refractive index copolymers of the present invention consist essentially of (i) one or more monomers having the structure:

$$CH_2=\overset{X}{\underset{|}{C}}-COO-(CH_2)_m-Y-Ar$$

wherein:

X is H or $CH_3$;

m is 0–10;

Y is nothing, O, S, or NR wherein R is H, $CH_3$, $C_nH_{2n+1}$ (n=1–10) iso $OC_3H_7$, $C_6H_5$, or $CH_2C_6H_5$;

Ar is any aromatic ring which can be unsubstituted or substituted with H, $CH_3$, $C_2H_5$, n—$C_3H_7$, iso—$C_3H_7$, $OCH_3$, $C_6H_{11}$, Cl, Br, $C_6H_5$, or $CH_2C_6H_5$;

and (ii) one or more monomers having the structure:

$$CH_2=\overset{X}{\underset{|}{C}}-\overset{O}{\underset{||}{C}}O-((CH_2)_nO)_m-[Ar-Z-Ar']_a-$$
$$-O-((CH_2)_{n'}O)_{m'}-\overset{O}{\underset{||}{C}}-\overset{X'}{\underset{|}{C}}=CH_2$$

wherein:

X, X' is independently H or $CH_3$;

n, n' are independently 2 or 3;

m, m' are independently 2–25;

Ar, Ar' are independently as defined above;

a is 1 or 2; and

Z is $C(CH_3)_2$ or $S(=O)_2$.

17 Claims, 1 Drawing Sheet

FOREIGN PATENT DOCUMENTS

| | | |
|---|---|---|
| 2 431 511 | 2/1980 | France . |
| 010968 | 8/1984 | Japan . |
| 122225 | 1/1985 | Japan . |
| 056236 | 10/1985 | Japan . |
| 218626 | 5/1986 | Japan . |
| 256540 | 10/1986 | Japan . |
| 299560 | 12/1989 | Japan . |
| 206932 | 2/1990 | Japan . |
| 225216 | 4/1991 | Japan . |
| 128060 | 5/1991 | Japan . |
| 06285147 | 4/1993 | Japan . |
| WO 96/28762 | 9/1996 | WIPO . |
| WO 96/28763 | 9/1996 | WIPO . |

OPHTHALMIC LENS POLYMERS

This application claims priority from co-pending provisional application, U.S. patent application Ser. No. 60/023,623, filed Aug. 9, 1996.

FIELD OF THE INVENTION

This invention related to polymers and their use in ophthalmic lenses, particularly intraocular lenses that can be inserted through small incisions.

BACKGROUND OF THE INVENTION

In response to the development of cataractous lenses, it has become common to replace the lens with an intraocular lens (IOL) in a surgical procedure. In order to reduce the trauma to the eye in cataract surgery, it is desirable to keep the incision through which the surgical procedure is conducted as small as possible. With the development of phacoemulsification surgery, in which the lens is fragmented by ultrasonic vibrations and the fragments aspirated through a small cannula, it has become possible to remove a lens through an incision no larger than 2–3 millimeters. However, since an IOL is typically at least six millimeters in diameter, an incision at least that large has to be made to permit the insertion of the IOL. In order to permit the use of the desirable small incision technique, various flexible, distortable, and inflatable IOLs have been devised.

Juergens, U.S. Pat. No. 4,619,662, discloses a collapsible intraocular lens with a hollow interior which can be evacuated to cause the lens to collapse to a relatively small size. The collapsed lens can then be inserted into the eye through a relatively small incision. After insertion, the interior of the lens is filled with an elastomer to expand the lens to the proper shape and dimension.

Mazzocco, U.S. Pat. No. 4,573,998, discloses a deformable intraocular lens that can be rolled, or folded to fit through a relatively small incision. The deformable lens is inserted while it is held in its distorted configuration, then released inside the chamber of the eye, whereupon the elastic property of the lens causes it to resume its molded shape. As suitable materials for the deformable lens, Mazzocco discloses polyurethane elastomers, silicone elastomers, hydrogel polymer compounds, organic or synthetic gel compounds and combinations thereof.

Keates et al., U.S. Pat. No. 4,619,657, disclose a flexible intraocular lens holder made from a flexible inert polymer, such as silicone rubber, which contains pockets for receiving individual lenses which are small enough to fit through a relatively small incision. The lens holder is folded or rolled and inserted through a small incision and thereafter several of the small lenses are inserted through the incision and into the pockets in the lens holder to form a composite intraocular lens.

Gasser et al., U.S. Pat. No. 5,224,957, disclose photopolymerizable compositions useful in forming an intraocular lens in situ. The compositions are delivered into the natural lens capsule or a thin plastic shell substitute and then polymerized. The reference compositions contain 90–99.99% by weight of a least one at least difunctional acrylic and/or methacrylic acid ester. Suitable acid esters include bisphenol A or bishydroxypolyalkoxy bisphenol A derivative lengthened with ethylene oxide or propylene oxide. Preferred acrylic and/or methacrylic acid esters include those having the formula:

$$CH_2=CH-COO-(CH_2(CH_2)_xO)_n-phenyl-C(CH_3)_2-phenyl-(O(CH_2)_yCH_2)_m-OOC-CH=CH_2$$

wherein n, m=1–5, and x, y=1–3.

There is a need for a material, with a relatively high refractive index, that can be used to form a flexible intraocular lens capable of being simply rolled or folded for insertion through a small incision.

SUMMARY OF THE INVENTION

This invention is directed to high refractive index copolymers consisting essentially of (i) one or more monomers having the structure:

$$CH_2=\overset{X}{\underset{|}{C}}-COO-(CH_2)_m-Y-Ar$$

wherein:
X is H or $CH_3$;
m is 0–10;
Y is nothing, O, S, or NR wherein R is H, $CH_3$, $C_nH_{2n+1}$ (N=1–10) iso $OC_3H_7$, $C_6H_5$, or $CH_2C_6H_5$;
Ar is any aromatic ring which can be unsubstituted or substituted with H, $CH_3$, $C_2H_5$, n—$C_3H_7$, iso—$C_3H_7$, $OCH_3$, $C_6H_{11}$, Cl, Br, $C_6H_5$, or $CH_2C_6H_5$;

and (ii) one or more monomers having the structure:

$$CH_2=\overset{X}{\underset{|}{C}}-\overset{O}{\underset{||}{C}}O-((CH_2)_nO)_m-[Ar-Z-Ar']_a-$$
$$-O-((CH_2)_{n'}O)_{m'}-\overset{O}{\underset{||}{C}}-\overset{X'}{\underset{|}{C}}=CH_2$$

wherein:
X, X' are independently H or $CH_3$;
n, n' are independently 2 or 3;
m, m' are independently 2–25;
Ar, Ar' are independently as defined above;
a is 1 or 2; and
Z is $C(CH_3)_2$ or $S(=O)_2$.

These copolymers can be used to form various types of ophthalmic lenses, including, but not limited to, intraocular lenses, contact lenses, spectacle lenses, lenses for optical instruments. For example, the copolymers defined above may be used to form intraocular lenses that have high refractive indexes, are flexible and transparent, can be inserted into the eye through a relatively small incision, and recover their original shape after insertion.

DETAILED DESCRIPTION OF THE INVENTION AND PREFERRED EMBODIMENTS

Figure 1:
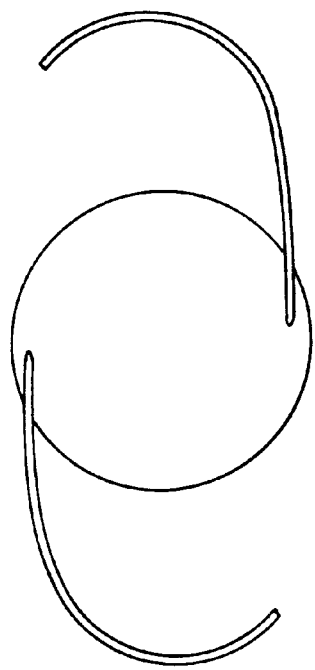
FIG. 1 shows a multipiece intraocular lens.

The high refractive index copolymers of the present invention consist essentially of (i) one or more monomers having the structure:

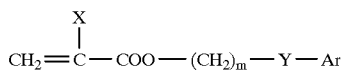

wherein:

X is H or $CH_3$;

m is 0–10;

Y is nothing, O, S, or NR wherein R is H, $CH_3$, $C_nH_{2n+1}$ (n=1–10) iso $OC_3H_7$, $C_6H_5$, or $CH_2C_6H_5$;

Ar is any romantic ring which can be unsubstituted or substituted with H, $CH_3$, $C_2H_5$, N—$C_3H_7$, iso—$C_3H_7$, $OCH_3$, $C_6H_{11}$, Cl, Br, $C_6H_5$, or $CH_2C_6H_5$;

and (ii) one or more monomers having the structure:

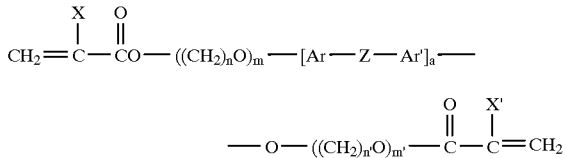

wherein:

X, X' are independently H or $CH_3$;

N, N' are independently 2 or 3;

m, m' are independently 2–25;

Ar, Ar' are independently as defined above;

a is 1 or 2; and

Z is $C(CH_3)_2$ or $S(=O)_2$.

Type (i) monomers are known and include, but are not limited to: 2-phenoxyethyl acrylate, 2-phenylethylthio acrylate, 2-phenylethylamino acrylate, phenyl acrylate, benzyl acrylate, 2-phenylethyl acrylate, 3-phenylpropyl acrylate, 4-phenylbutyl acrylate, 4-methylphenyl acrylate, 4-methylbenzyl acrylate, 2-2-methlphenylethyl acrylate, 2-3-methylphenylethyl acrylate, 2-4-methylphenylethyl acrylate, and the like, including their corresponding methacrylates. These acrylic/methacrylic monomers and others are disclosed in U.S. Pat. No. 5,290,892, the entire contents of which are hereby incorporated by reference.

Preferred monomers of type (i) are those where X is H; m is 2–4; Y is nothing or O; and Ar is phenyl. Most preferred are 2-phenylethyl acrylate, 2-phenoxyethyl acrylate, 3-phenylpropyl acrylate, 3-phenoxypropyl acrylate, 4-phenylbutyl acrylate, and 4-phenoxybutyl acrylate.

The amount of type (i) monomer present in the high refractive index copolymers of the present invention will vary depending upon the identity of the type (i) monomer(s), the identity of the type (ii) monomer(s) and the mechanical properties desired for the final copolymer. For example, foldable intraocular lenses are preferably made from polymers having a glass transition temperature no greater then normal room temperature, e.g., about 20° C., in order that the lenses can be rolled or folded conveniently at room temperature. Additionally, copolymers exhibiting an elongation of at least 150% are preferred for use in foldable intraocular lenses because such lenses must exhibit sufficient strength to allow them to be folded without fracturing. More preferred for foldable intraocular lens applications are polymers having an elongation of at least 200%. Thus, for foldable intraocular lens applications, the copolymers of the present invention will generally contain at least about 60% by weight, preferably at least about 80% by weight, of the type (i) monomer(s).

Type (ii) monomers can be synthesized using known methods and many are commercially available from a variety of sources (e.g., Dajac Laboratories, Inc. (Feasterville, PA). Preferred type (ii) monomers are those where n and n' are 2; m and m' are independently 2–12; Ar and Ar' are phenyl; Z is $C(CH_3)_2$; and a is 1. Most preferred is the type (ii) monomer where X=X'=H, n=n'=2, m=m'=2, Ar=Ar'=phenyl, a=1, and Z=$C(CH_3)_2$ [hereinafter referred to as "Ethoxylated (4 moles) bisphenol A diacrylate"].

As in the case of the monomer of type (i), the amount of type (ii) monomer present in the high refractive index copolymers of the present invention will vary depending upon the identity of the type (i) monomer(s), the identity of the type (ii) monomer(s), and the mechanical properties desired for the final copolymer. In general, for foldable intraocular lens applications, the copolymers of the present invention will contain from about 10 to about 40% by weight, preferably from about 10 to about 20% by weight, of the type (ii) monomer(s).

For foldable intraocular lens applications, if the type (i) monomer is chosen to be a methacrylate derivative, then m and m' in the type (ii) monomer will be relatively large. On the other hand, if the type (i) monomer is chosen to be an acrylate derivative, then m and m' in the type (ii) monomer will be relatively small in order to achieve a flexible, foldable copolymeric material.

Although not essential, the copolymers of the present invention may optionally contain one or more of a variety of other ingredients, such as polymerization initiators, copolymerizable cross-linking monomers, and copolymerizable UV- or blue-light blocking chromophores. Polymerization initiators may be, for example, thermal or light-activated initiators.

Typical thermal free radical initiators include peroxides, such as benzophenone peroxide, peroxycarbonates, such as bis-(4-t-butylcyclohexyl) peroxydicarbonate, azonitriles, such as azobisisobytyronitrile, and the like. Preferred initiators are bis-(4-t-butylcyclohexyl) peroxydicarbonate and t-butyl peroxy-2-ethyl hexanoate ("t-butyl-peroctoate"). Alternately, the monomers can be photopolymerized by using a mold which is transparent to radiation of a wavelength capable of initiating polymerization of these acrylic monomers by itself. For materials lacking UV-absorbing chromophores, conventional photoinitiator compounds, e.g., a benzophenone-type photoinitiator, can also be introduced to facilitate the polymerization. Photosensitizers can be introduced as well to permit the use of longer wavelengths; however, in preparing a polymer which is intended for long residence within the eye, it is generally preferable to keep the number of ingredients in the polymer to a minimum to avoid the presence of materials which might leach from the lens into the interior of the eye.

If desired, suitable cross-linking monomers include almost any terminally ethylenically unsaturated compound having more than one unsaturated group. Suitable cross-linking agents include, for example: ethylene glycol dimethacrylate, diethylene glycol dimethacrylate, allyl methacrylate, 1,3-propanediol dimethacrylate, allyl methacrylate, 1,6-hexanediol dimethacrylate, 1,4-butanediol dimethacrylate, and the like. A preferred cross-linking agent is 1,4-butanediol diacrylate (BDDA).

Ultraviolet and/or blue-light absorbing chromophores can also be included in the copolymers of the present invention, as may be desirable in the case where the copolymers are used to make intraocular lenses. Such chromophores allow the light absorbance of an intraocular lens to approximate that of the eye's natural lens. The ultraviolet absorbing material can be any compound which absorbs ultraviolet light, i.e., light having a wavelength shorter than about 400 nm, but does not absorb any substantial amount of visible light. The ultraviolet absorbing compound is incorporated into the monomer mixture and is entrapped in the polymer matrix when the monomer mixture is polymerized. Suitable ultraviolet absorbing compounds include substituted benzophenones, such as 2-hydroxybenzophenone, and 2-(2-hydroxphenyl)-benzotriazoles. It is preferred to use an ultraviolet absorbing compound which is copolymerizable with the type (i) and (ii) monomers described above and is thereby covalently bound to the polymer matrix. In this way possible leaching of the ultraviolet absorbing compound out of the lens and into the interior of the eye is minimized. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,526,311. The most preferred ultraviolet absorbing compound is 2-(3'-methallyl-2'-hydroxy-5'-methyl phenyl) benzotriazole.

As in the case of UV-absorbers, it is preferred to use blue-light absorbing compounds which are coplymerizable with the type (i) and type (ii) monomers. Suitable polymerizable blue-light blocking chromophores include those disclosed in U.S. Pat. No. 5,470,932.

The copolymers of this invention are prepared by generally conventional polymerization methods. For example, a mixture of the liquid monomers in the desired proportions together with a conventional thermal free-radical initiator is prepared. The mixture can then be introduced into a mold of suitable shape to form an ophthalmic lens, and the polymerization carried out by gentle heating to activate the initiator.

Intraocular lenses (IOLs) constructed of the disclosed polymers can be of any designs capable of being rolled or folded into a small cross section that can fit through a relatively smaller incision. For example, the IOLs can be of what is known as a one piece or multipiece design. Typically, an IOL comprises an optic and at least one haptic. The optic is that portion which serves as the lens and the haptics are attached to the optic and are like arms which hold the optic in its proper place in the eye. The optic and haptic(s) can be of the same or different material. A multipiece lens, as shown in FIG. 1, is so called because the optic and the haptic(s) are made separately and then the haptics are attached to the optic. Haptics may be attached to the optic using conventional techniques. In a single piece lens, the optic and the haptics are formed out of one piece of material. Depending on the material, the haptics are then cut, or lathed, out of the material to produce the IOL.

Figure 2:
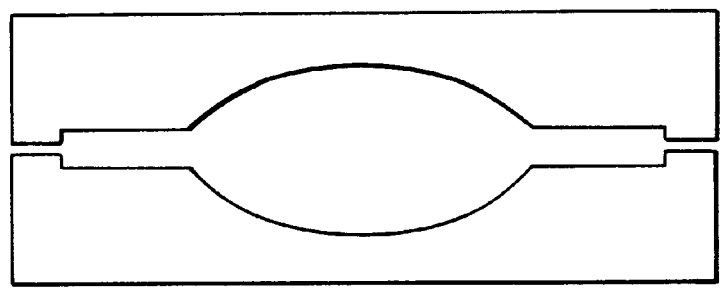
FIG. 2 shows a cross-section of a mold for making intraocular lenses.

Molding and drilling operations are easily carried out if the optic is molded between two polypropylene mold halves as shown in FIG. 2. The mold containing the cured optic material is then placed on a lathe and the desired optic diameter is lathe out. The mold may then be easily mounted to carry out any drilling operations prior to removing the mold halves. Both the lathing and drilling operations may be facilitated by cooling the mold/optic in a freezer to less than 10° C. and preferably less that 0° C. prior to each of these operations.

The invention will be further illustrated by the following examples which are intended to be illustrative, but not limiting.

EXAMPLES

The mixtures of Examples –3, shown in Table 1 below, were each transferred into two molds: (i) an IOL mold of the type illustrated in FIG. 1 and (ii) a slab mold made of two polypropylene plates. The filled molds were clamped with spring clamps and cured in an oven for 2 hours at 80° C. and 2 hours at 110° C. At the end of the polymerization period, the molds were allowed to cool to room temperature. The molds were then opened and the cured intraocular lens and sheet of polymer were removed.

TABLE 1

| Ingredient | Example # | | |
|---|---|---|---|
| | 1 | 2 | 3 |
| 2-Phenylethyl acrylate | 89.6* | 83.2 | 76.2 |
| Ethoxylated (4 moles) Bisphenol A Diacrylate | 10.0 | 17.2 | 24.3 |
| o-Methallyltinuvin P | 0.8 | 0.6 | 0.6 |
| t-butyl peroctoate | 1 | 1 | 1 |

*All values are expressed as parts by weight.

The physical properties of the cured lenses and slabs, shown in Table 2 below, were analyzed (room temperature conditions) as follows: the glass transition temperature ($T_g$) was measured by differential thermal analysis using conventional equipment. The Secant Modulus (psi), tensile strength (psi), and ultimate elongation (% strain) were determined using an Instron Model 1122 Material Tester for a dumbell-shaped sample of material. The refractive index was measured with an Abbe refractometer.

TABLE 2

| Physical Property | Example # | | |
|---|---|---|---|
| | 1 | 2 | 3 |
| $T_g$ (° C.) | 7.2 | 11.5 | 15.2 |
| Secant Modulus (psi) | 78 | 175 | 390 |
| Tensile Strength (psi) | 570 | 661 | 1256 |
| % Strain | 575 | 335 | 339 |
| Refractive Index | 1.5575 | 1.5579 | 1.5587 |

The invention having now been fully described, it should be understood that i may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. A copolymer consisting essentially of (i) a total of at least 60% (w/w) of one or more monomers having the structure:

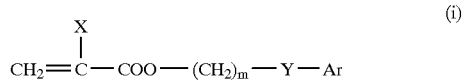

(i)

wherein:
X is H;
n is 0–10;
Y is nothing, O, S, or NR wherein R is H, $CH_3$, $C_nH_{2n+1}$ (n=1–10) iso $OC_3H_7$, $C_6H_5$, or $CH_2C_6H_5$;
Ar is any aromatic ring which can be unsubstituted or substituted with $CH_3$;

$C_2H_5$, n—$C_3H_7$, iso—$C_3H_7$, $OCH_3$, $C_6H_{11}$, Cl, Br, $C_6H_5$, or $CH_2C_6H_5$;

and (ii) a total of at least 10% (w/w) of one or more monomers having the structure:

$$CH_2=\overset{X}{\underset{|}{C}}-\overset{O}{\underset{\|}{C}}O-((CH_2)_nO)_m-[Ar-Z-Ar']_a- \quad \text{(ii)}$$

$$-O-((CH_2)_{n'}O)_{m'}-\overset{O}{\underset{\|}{C}}-\overset{X'}{\underset{|}{C}}=CH_2$$

wherein:

X, X' are H;

n, n' are independently 2 or 3;

m, m' are independently 2–25;

Ar, Ar' are independently as defined above;

a is 1 or 2; and

Z is $C(CH_3)_2$ or $S(=O)_2$;

provided that the copolymer has a $T_g$ no greater than about 20° C. and an elongation of at least 150% at about 20° C.

2. The copolymer of claim 1 wherein the monomer(s) of structure (i) have n=2–4; Y=nothing or O; and Ar=phenyl.

3. The copolymer of claim 2 wherein the monomer(s) of structure (i) are selected from the group consisting of 2-phenylethyl acrylate, 2-phenoxyethyl acrylate, 3-phenylpropyl acrylate, 3-phenoxypropyl acrylate, 4-phenylbutyl acrylate, and 4-phenoxybutyl acrylate.

4. The copolymer of claim 1 wherein the monomer(s) of structure (ii) have n and n'=2; m and m' independently= 2–12; Ar and Ar'=phenyl; Z=$C(CH_3)_2$; and a is 1.

5. The copolymer of claim 4 wherein m and m'=2.

6. The copolymer of claim 2 wherein the monomer(s) of structure (ii) have n and n'=2; m and m' independently= 2–12; Ar and Ar'=phenyl; Z=$C(CH_3)_2$; and a is 1.

7. The copolymer of claim 1 wherein the total amount of the monomer(s) of structure (i) is at least about 80% (w/w).

8. The copolymer of claim 1 further comprising an ingredient selected from the group consisting of polymerization initiators, copolymerizable cross-linking monomers, and copolymerizable UV- and blue-light-blocking chromophores.

9. An ophthalmic lens consisting essentially of (i) a total of at least 60% (w/w) of one or more monomers having the structure:

$$CH_2=\overset{X}{\underset{|}{C}}-COO-(CH_2)_m-Y-Ar \quad \text{(i)}$$

wherein:

X is H;

n is 0–10;

Y is nothing, O, S, or NR wherein R is H, $CH_3$, $C_nH_{2n+1}$ (n=1–10) iso $OC_3H_7$, $C_6H_5$, or $CH_2C_6H_5$;

Ar is any aromatic ring which can be unsubstituted or substituted with $CH_3$;

$C_2H_5$, n—$C_3H_7$, iso—$C_3H_7$, $OCH_3$, $C_6H_{11}$, Cl, Br, $C_6H_5$, or $CH_2C_6H_5$;

and (ii) a total of at least 10% (w/w) of one or more monomers having the structure;

$$CH_2=\overset{X}{\underset{|}{C}}-\overset{O}{\underset{\|}{C}}O-((CH_2)_nO)_m-[Ar-Z-Ar']_a- \quad \text{(ii)}$$

$$-O-((CH_2)_{n'}O)_{m'}-\overset{O}{\underset{\|}{C}}-\overset{X'}{\underset{|}{C}}=CH_2$$

wherein:

X, X' are H;

n, n' are independently 2 or 3;

m, m' are independently 2–25;

Ar, Ar' are independently as defined above;

a is 1 or 2; and

Z is $C(CH_3)_2$ or $S(=O)_2$, provided that the copolymer has a $T_g$ no greater than about 20° C. and an elongation of at least 150% at about 20° C.

10. The ophthalmic lens of claim 9 wherein the monomer(s) of structure (i) have n=2–4; Y=nothing or O; and Ar=phenyl.

11. The ophthalmic lens of claim 10 wherein the monomer(s) of structure (i) are selected from the group consisting of 2-phenylethyl acrylate, 2-phenoxyethyl acrylate, 3-phenylpropyl acrylate, 3-phenoxypropyl acrylate, 4-phenylbutyl acrylate, and 4-phenoxybutyl acrylate.

12. The ophthalmic lens of claim 9 wherein the monomer (s) of structure (ii) have n and n'=2; m and m' independently=2–12; Ar and Ar'=phenyl; Z=$C(CH_3)_2$; and a is 1.

13. The ophthalmic lens of claim 12 wherein m and m'=2.

14. The ophthalmic lens of claim 10 wherein the monomer(s) of structure (ii) have n and n'=2; m and m' independently =2–12; Ar and Ar'=phenyl; Z=$C(CH_3)_2$; and a is 1.

15. The ophthalmic lens of claim 9 wherein the total amount of the monomer(s) of structure (i) is at least about 80% (w/w).

16. The ophthalmic lens of claim 9 further comprising an ingredient selected from the group consisting of polymerization initiators, copolymerizable cross-linking monomers, and copolymerizable UV- and blue-light-blocking chromophores.

17. The ophthalmic lens of claim 9 wherein the ophthalmic lens is an intraocular lens optic.

* * * * *